US00PP11742P2

(12) United States Plant Patent
Osiecki

(10) Patent No.: US PP11,742 P2
(45) Date of Patent: Jan. 16, 2001

(54) ANTHURIUM PLANT NAMED 'ATWELVE'

(75) Inventor: Marian W. Osiecki, Marianna, FL (US)

(73) Assignee: Oglesby Plants Intl., Inc., Altha, FL (US)

( * ) Notice: Under 35 U.S.C. 154(b), the term of this patent shall be extended for 0 days.

(21) Appl. No.: 09/292,198

(22) Filed: Apr. 15, 1999

(51) Int. Cl.[7] ..... A01H 5/00
(52) U.S. Cl. ..... Plt./365
(58) Field of Search ..... Plt./369, 365, 367, Plt./368

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Anthurium named 'Atwelve' particularly characterized by its dwarf growth habit; good vigor; early and year-round flowering; floriferousness; large spathes, that is, large relative to plant size, with very good longevity; red-colored spathes and contrasting lighter colored spadices; and straight, thick and strong peduncles that hold spathes above or just at the foliar plane.

2 Drawing Sheets

BACKGROUND OF THE INVENTION

The present invention relates to a new and distinct cultivar of Anthurium plant, botanically known as Anthurium hybrid, and hereinafter referred to by the cultivar name Atwelve.

The new Anthurium is a product of a planned breeding program conducted by the Inventor in Altha, Fla. The objective of the breeding program was to develop early-flowering and dwarf pot Anthuriums with attractive spathe and spadix colors.

The new Anthurium originated from a cross made by the Inventor in 1993, in Altha, Fla., of a proprietary seedling selection of Anthurium hybrid code number 91-94-2 as the male, or pollen, parent with the Anthurium hybrid cultivar A2, disclosed in U.S. Plant Pat. No. 10,210, as the female, or seed, parent. The cultivar Atwelve was discovered and selected by the Inventor in 1994 as a seedling within the progeny of the stated cross in a controlled environment in Altha, Fla.

Plants of the new Anthurium are distinguished from plants of the parent cultivar A2 primarily in spathe color. In addition, plants of the new Anthurium differ from plants of the parent cultivar A2 in the following characteristics:

1. Plants of the new Anthurium have slightly darker green leaves than plants of the cultivar A2.
2. Plants of the new Anthurium flower slightly earlier than plants of the cultivar A2.
3. Spathes of the new Anthurium are slightly larger and more deltoid in shape than spathes of the cultivar A2.

Asexual propagation of the new cultivar by tissue culture in Altha, Fla. has shown that the unique features of this new Anthurium plant are stable and reproduced true to type in successive generations.

SUMMARY OF THE INVENTION

The new Anthurium has not been observed under all possible environmental conditions. The phenotype may vary somewhat with variations in environment such as temperature, light intensity, fertilizer rate, irrigation amount and frequency, and/or propagation procedures without, however, any variance in genotype.

The following traits have been repeatedly observed and are determined to be the unique characteristics of 'Atwelve'. These characteristics in combination distinguish 'Atwelve' as a new and distinct cultivar:

1. Plants of the new Anthurium are dwarf; appropriate for 7.5 to 15-cm containers.
2. Plants of the new Anthurium grow very vigorously.
3. Plants of the new Anthurium are extremely early flowering; flowers typically develop about 9 to 10 months after planting of tissue culture-produced microcuttings.
4. Plants of the new Anthurium produce numerous spathes and flower year-round.
5. Plants of the new Anthurium have large spathes, that is, large in relation to plant size, with very good longevity.
6. Plants of the new Anthurium have red-colored spathes and contrasting lighter colored spadices. With subsequent development spathes gradually become pink with increasing green, but retain ornamental value for several months past maturity.
7. Spathes are held above or at the foliage level on straight, thick and strong peduncles.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the first sheet comprises a top perspective view of a typical plant of 'Atwelve' in a 10-cm container about 11.5 months after planting a single tissue culture-produced microcutting.

The photograph at the bottom of the first sheet comprises a close-up view of a typical mature spathe and spadix.

The photograph at the top of the second sheet comprises a close-up view of the upper surface of a typical fully expanded leaf.

The photograph at the bottom of the second sheet comprises a close-up view of the lower surface of a typical fully expanded leaf. Spathe, spadix and leaf colors in the photographs may appear different from the actual colors due to light reflectance.

DETAILED BOTANICAL DESCRIPTION

The following observations and measurements were recorded in September, 1997, on plants grown in Altha, Fla. under greenhouse conditions which closely approximate those used in commercial horticultural practice. Plants used for this description were grown as single plants in 10-cm containers and were about 10.5 months from planting a tissue culture-produced microcutting. Older plants may differ in some morphological characteristics such as leaf and spathe shape. Fully developed plant structures and organs were used for the following observations and measurements unless otherwise indicated. Color values were determined on Sep. 18, 1997 in a greenhouse with a light level of about 600 to 830 foot-candles.

In the following description, color references are made to The Royal Horticultural Society Colour Chart except where general terms of ordinary dictionary significance are used. Numerical measurements represent averages from typical plants of 'Atwelve'.

Botanical classification: Anthurium hybrid cultivar Atwelve.

Parentage:

*Male, or pollen, parent.*—Proprietary seedling selection of Anthurium hybrid code number 91-94-2.

*Female, or seed, parent.*—Anthurium hybrid cultivar A2, disclosed in U.S. Plant Pat. No. 10,210.

Propagation:

*Type.*—By tissue culture.

*Time to initiate roots.*—Summer: About 21 days at about 25 to 30° C. soil temperature. Winter: About 28 days at about 22 to 27° C. soil temperature.

*Time to produce a rooted liner.*—Summer: About 16 to 18 weeks at about 25 to 30° C. soil temperature. Winter: About 18 to 20 weeks at about 22 to 27° C. soil temperature.

*Root characteristics.*—Fleshy; branching; cream to light pink to dark red with yellow root caps.

Plant description:

*Growth habit.*—Dwarf with a short main stem, open plant form. Appropriate for 7.5 to 15-cm containers.

*Plant size.*—Height, soil surface to top of leaf canopy: About 11.8 cm. Height, soil surface to top of spathes: About 13.8 cm. Width: About 26.2 cm.

*Plant vigor.*—Vigorous.

*Crop time.*—Plants grown in 10-cm containers begin flowering about 9 to 10 months after planting tissue culture-produced microcuttings. At about 10.5 months after planting, plants of the new Anthurium typically have developed two or three spathes above or among the leaves.

*Leaf blade.*—Number: About 9. Shape: Ovate, slightly asymmetrical. Apex: Long, acuminate, slightly curved. Base: Truncate during early plant development; leaf bases become slightly more cordate with subsequent plant development. Margin: Entire. Length, mature leaves: About 11.9 cm. Width, mature leaves: About 6.8 cm. Length to width ratio, mature leaves: About 1.8 to 1. Aspect: Midrib of most leaf blades close to horizontal or apex slightly upright; lobes curve upward, most pronounced on leaves of older plants. Texture: Thick, leathery, smooth. Surface: Slightly glossy, younger leaves more glossy than older leaves. Veins: Prominent near leaf base, less conspicuous near apex. Color: Newly unrolled leaf, upper surface: More brown and much darker than 148A. Newly unrolled leaf, lower surface: Darker and slightly more brown than 148A; most veins, red purple; red purple band less than 1 mm wide at margins. Mature leaf, upper surface: 147A; veins in the proximal half of the blade close to 144A; veins in the distal half not distinct, slightly lighter or similar color as surrounding tissue. Mature leaf, lower surface: 147B.

*Petiole.*—Length: About 8.2 cm. Diameter, below geniculum: About 2.8 cm. Geniculum: Inconspicuous; about 8 mm in length and about 3.3 mm in diameter at the base. Petiole wings: Inconspicuous; about 1.1 cm in length. Color: Newly unrolled leaves: Color not available in R.H.S. Colour Chart, however close to grayed-orange, 166A, 165A and 175A; back lighter than front; distal 5 to 6 mm, occasionally green. Fully expanded leaves: Geniculum, front surface: 146A to 146B. Geniculum, back surface: 146C. Below geniculum, front surface: 146A to 146B. Below geniculum, back surface: 146B; proximally progressively darker, 146A or 147B at wing tips; base, 146B to 146C.

Inflorescence description:

*Inflorescence arrangement.*—Spathes with spadices held above or just at the foliar plane on straight, strong and thick peduncles. Flowering structures arise from leaf axils. Freely flowering; numerous spathes/spadices per plant; extremely early and continuous flowering year-round. Large spathes, that is, large relative to plant size; ratio spathe length to spadix length about 1.5 to 1.

*Inflorescence longevity.*—Spathes maintain red coloration for about 9 to 10 weeks following appearance of bud above or among the foliage; red coloration gradually fades to pink with increasing areas of green. Spathes continue to enhance ornamental value of the new Anthurium for several months past maturity; persistent.

*Flowers/reproductive organs.*—Quantity per spadix: Numerous, about 7 to 8 flowers per linear centimeter of spadix (mid-section). Perianth: Visible between pistils. Pistil: Small, white, translucent; stigma, minute. Stamens: Not visible; no pollen produced.

*Spathe.*—Length: About 4.6 cm. Width: About 4.6 cm. Length to width ratio: About 1 to 1. Shape: Deltoid with ovate tendencies. Apex: Between aristate and mucronate; about 2 to 3 mm in length. Base: Cordate to almost truncate; occasionally slightly asymmetric; lobes typically extend slightly beyond peduncle. Margin: Entire. Texture: Smooth and leathery with various degrees of puckering. Slightly glossy, less so with development. Back surface glossier than front surface. Aspect: Mostly horizontal. Color: Closed bud: Close to 53B with green veins; occasionally basal area near margin slightly lighter with some green coloration. Newly unrolled spathe (without any developed pistils), front surface: 53B to 53C; inconspicuous darker red band, about 1 mm wide, at margins; apex, light green. Newly unrolled spathe (without any developed pistils), back surface: Close to 53B; dark green veins; very glossy; apex, light green. Mature spathe (pistils fully developed on about 50 to 75 percent of spadix), front surface: 53B to 53C; inconspicuous darker red band, about 1 mm wide, at margins; apex, light green. Mature spathe (pistils fully developed on about 50 to 75 percent of spadix), back surface: Close to 53B; dark green veins; glossy; apex, light green.

*Spadix.*—Length: About 3.1 cm. Diameter: About 6.1 mm. Shape: Columnar, slightly tapering at apex. Cross section: Rounded. Aspect: About 65 to 90 degrees to spathe. Color: Young: Proximal, 158C to 158D with red purple dots from which pistils eventually emerge. In some regions red purple dots may dominate the yellowish white background. Distal, more yellow with dots less conspicuous. Apex, predominantly yellow, close to 11B. Mature: Proximal, 50 to 75 percent with developed pistils, close to 158D. Red purple dots, close to 63C, are visible at various distances from base. Dots most pronounced in zone of emerging pistils. Distal, dots less conspicuous, mostly yellow orange, close to 23C, and/or yellow, 11A to 11B, predominate. With subsequent development, entire spadix becomes cream-colored with occasional irregular areas of pink.

*Peduncle.*—Length: About 10.3 cm. Diameter, just below spathe: Thick, about 2.7 mm. Stipe: About 2.5 mm in length. Aspect: Strong and erect. Color: Front surface: 147A above spathe; 146A below spathe. Back surface: 146A to 146B.

Disease/insect resistance: Plants of the new Anthurium have not been shown to be unusually susceptible to pathogens and insects common to Anthurium.

Seed development: Seed development on plants of the new Anthurium has not been observed.

It is claimed:

1. A new and distinct cultivar of Anuthurium plant named 'Atwelve', as illustrated and described.

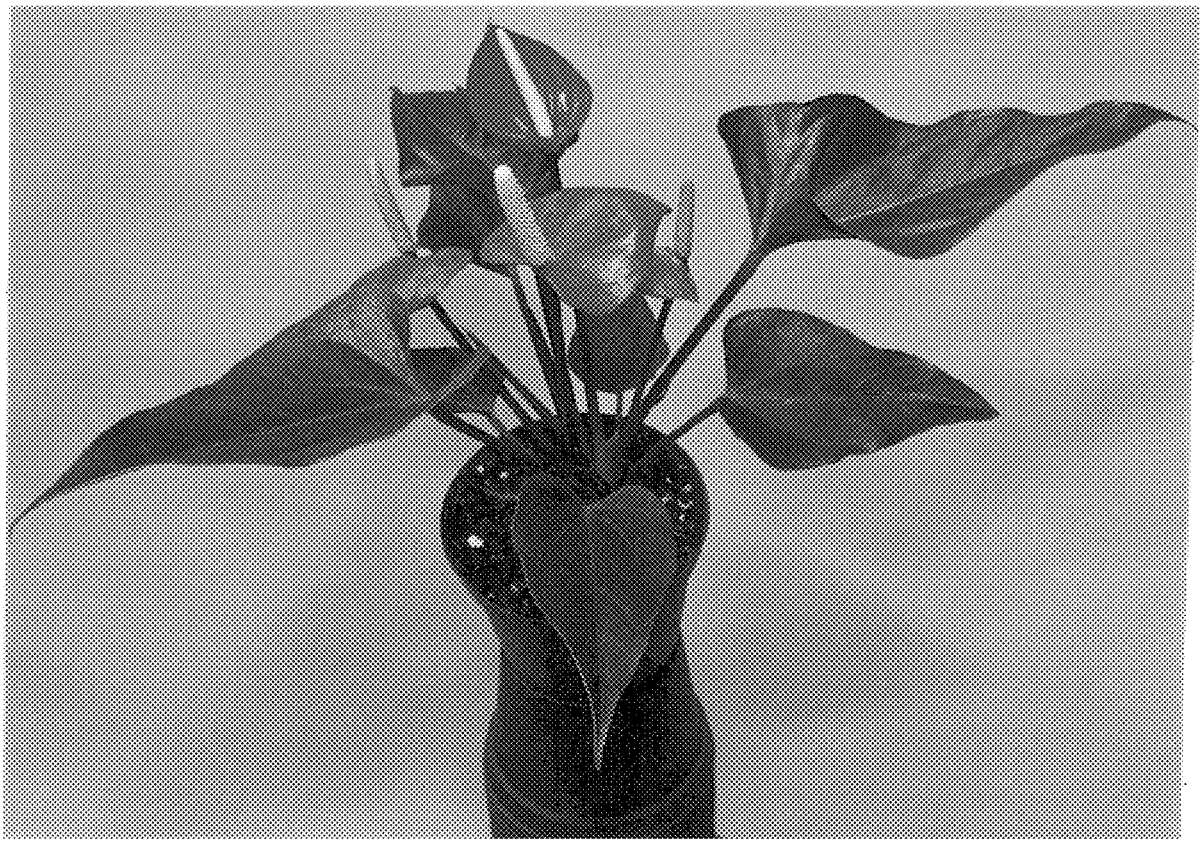
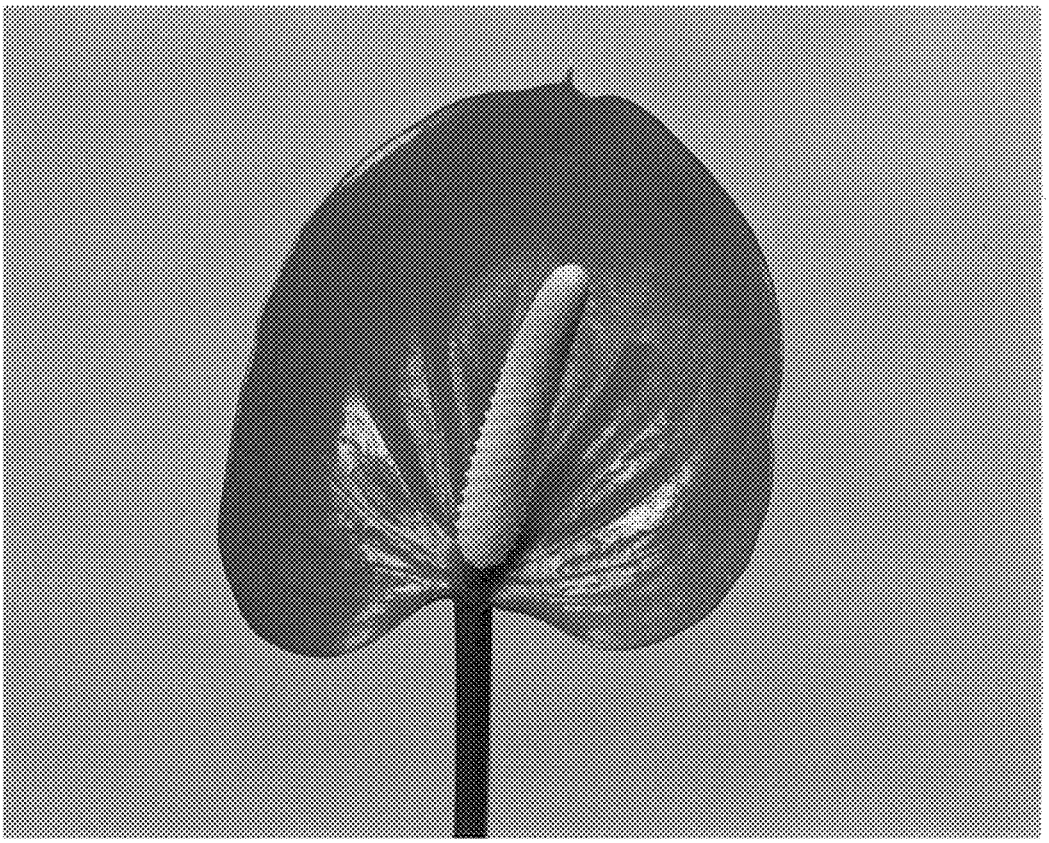

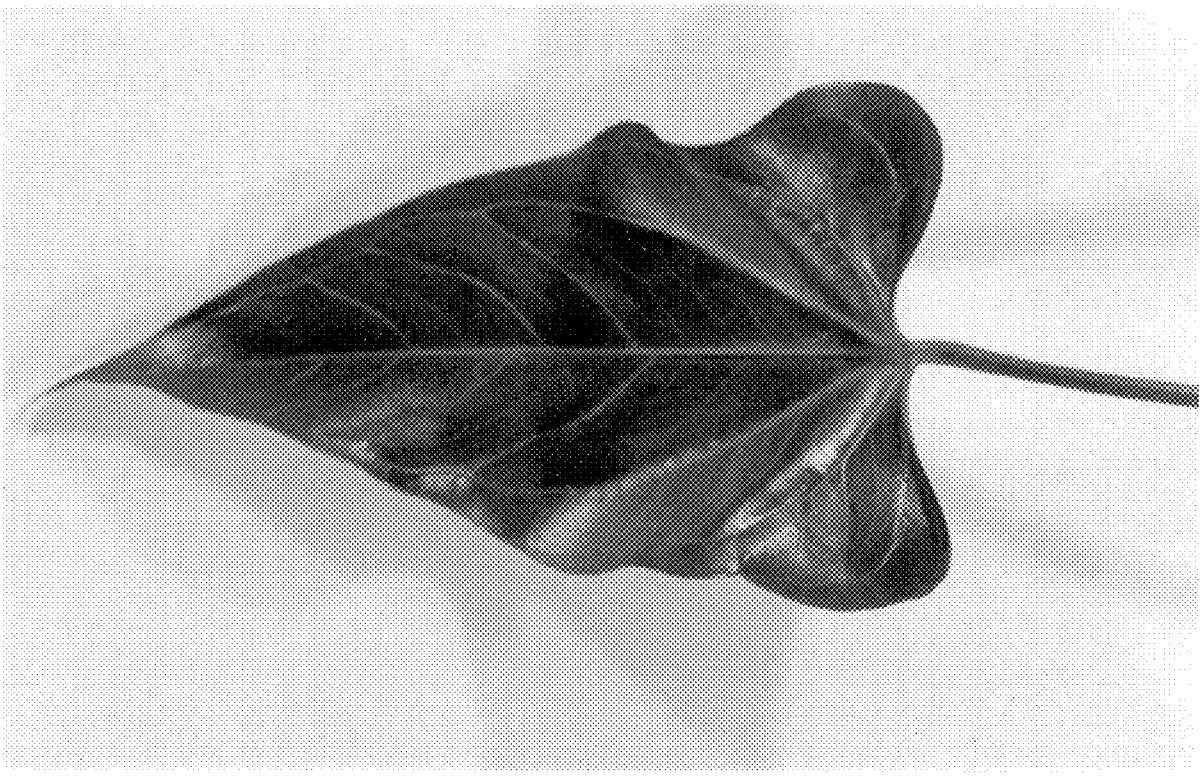
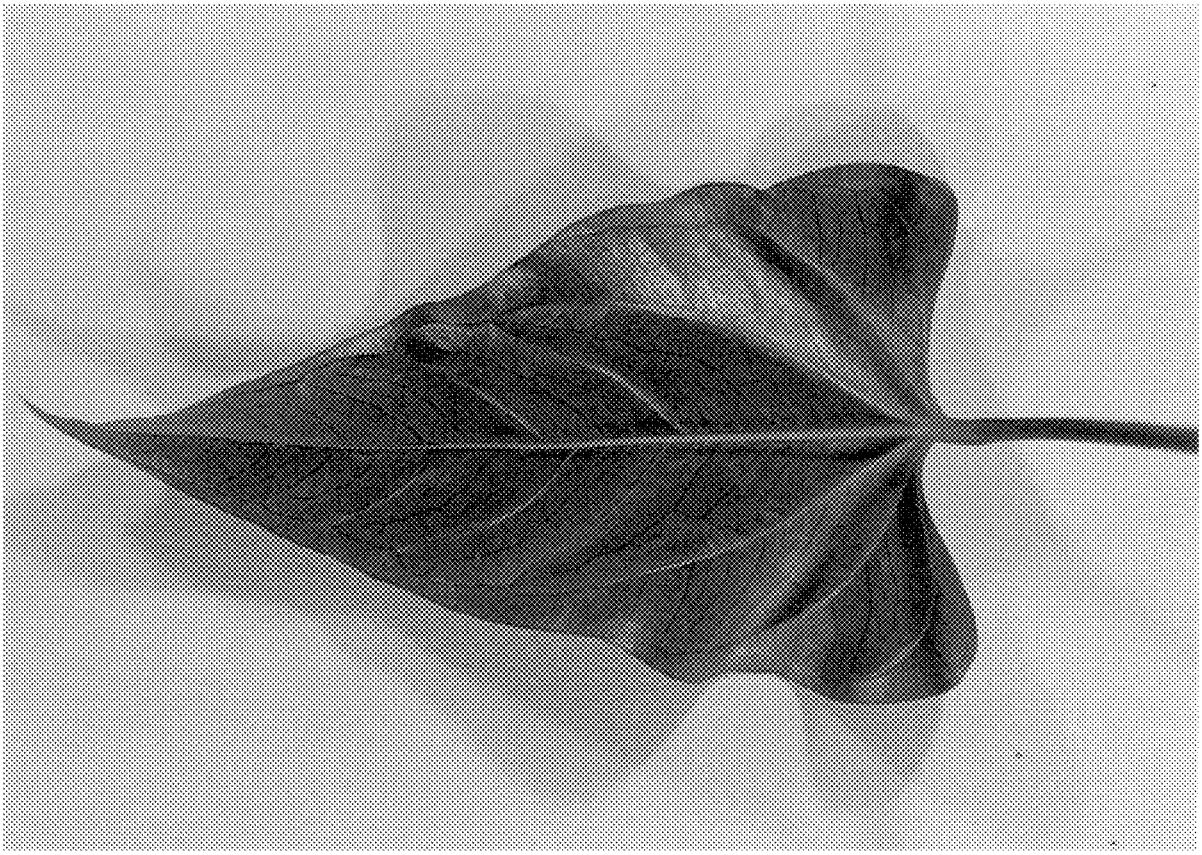

* * * * *